United States Patent [19]

Karlson

[11] 4,107,041

[45] Aug. 15, 1978

[54] ELECTROMATOGRAPHIC SEPARATING APPARATUS AND SYSTEM

[76] Inventor: Eskil Karlson, P.O. Box 9000, Stamford, Conn. 06902

[21] Appl. No.: 783,208

[22] Filed: Mar. 31, 1977

[51] Int. Cl.$^2$ ............................................. B01D 15/08
[52] U.S. Cl. ................................. 210/198 C; 55/197; 55/390; 210/267; 210/378
[58] Field of Search .......................... 55/67, 197, 390; 210/198 C, 267, 378

[56] References Cited

U.S. PATENT DOCUMENTS

| | | | |
|---|---|---|---|
| 1,828,548 | 10/1931 | Shapley | 210/378 X |
| 2,138,861 | 12/1938 | Hyman | 210/267 X |
| 3,078,647 | 2/1963 | Mosier | 55/197 |
| 3,503,712 | 3/1970 | Sussman | 210/198 C |
| 3,782,078 | 1/1974 | Jeape | 55/197 |
| 3,856,669 | 12/1974 | Ito et al. | 210/198 C |

*Primary Examiner*—John Adee

[57] ABSTRACT

A continuous chromatographic separation is effected by a column packed with finely divided chromatographic particles, the nature of which depends on the materials to be separated. In the case of liquid systems, the cylinder containing chromatographic packing is substantially horizontal and is spun to develop substantial centrifugal force. Preferably, the cylinder is of suitable porous material, such as a ceramic of the type used for filtration. The liquid, having dissolved or suspended therein the constituents to be separated, is introduced at one end under substantial pressure, for example by a pump, which, preferably, rotates with the cylinder. The cylinder is supported along its length by non-corrosive, such as stainless steel, rings. The rings are held together by through-bolts and, if necessary, spacers. In the case of a porous ceramic cylinder, the pores are small, and there are stationary troughs at the peripheries of each pair of rings which receive liquid coming out. For horizontal cylinders there are drain holes in the lower trough which permit the liquid to go into collectors at predetermined points along the cylinder. The sample, which is introduced under some pressure, moves along the chromatographic packing, and separation of various constituents is effected chromatographically.

In the case of gas chromatography, the cylinder may be of metal with suitable rows of openings along the periphery of segments formed by supporting rings.

10 Claims, 7 Drawing Figures

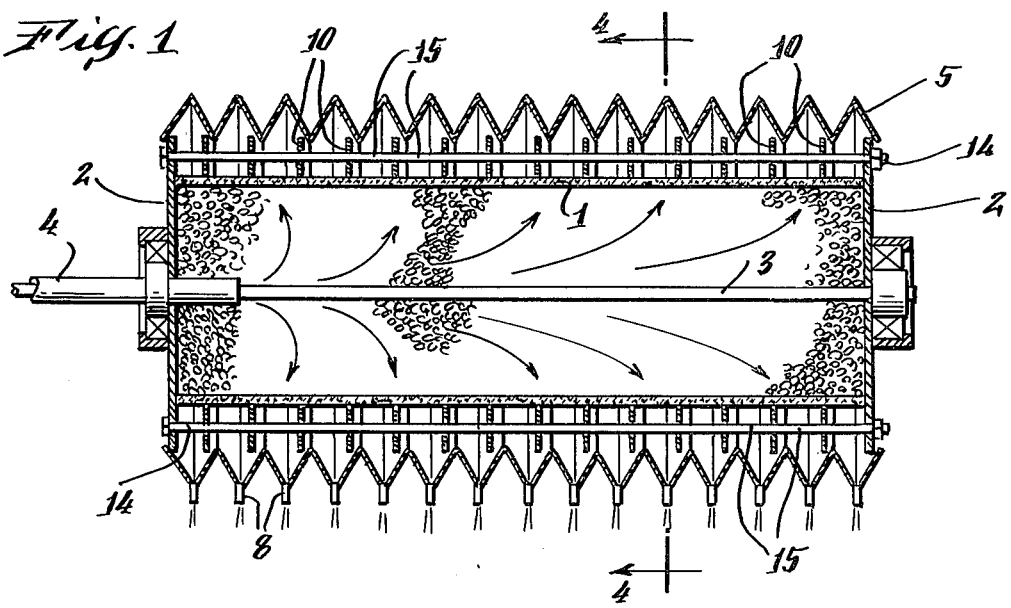
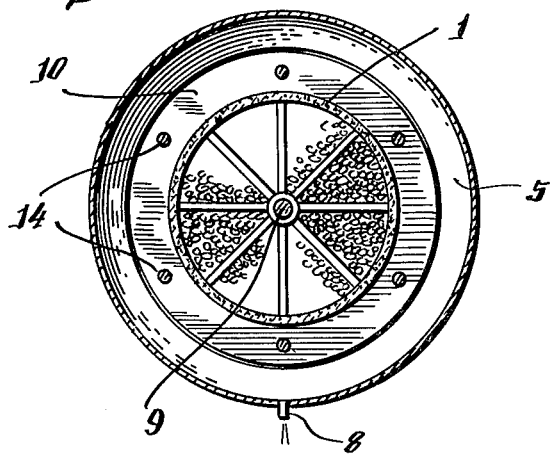
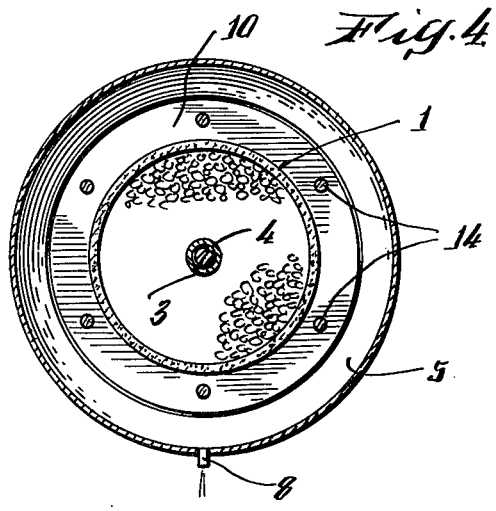
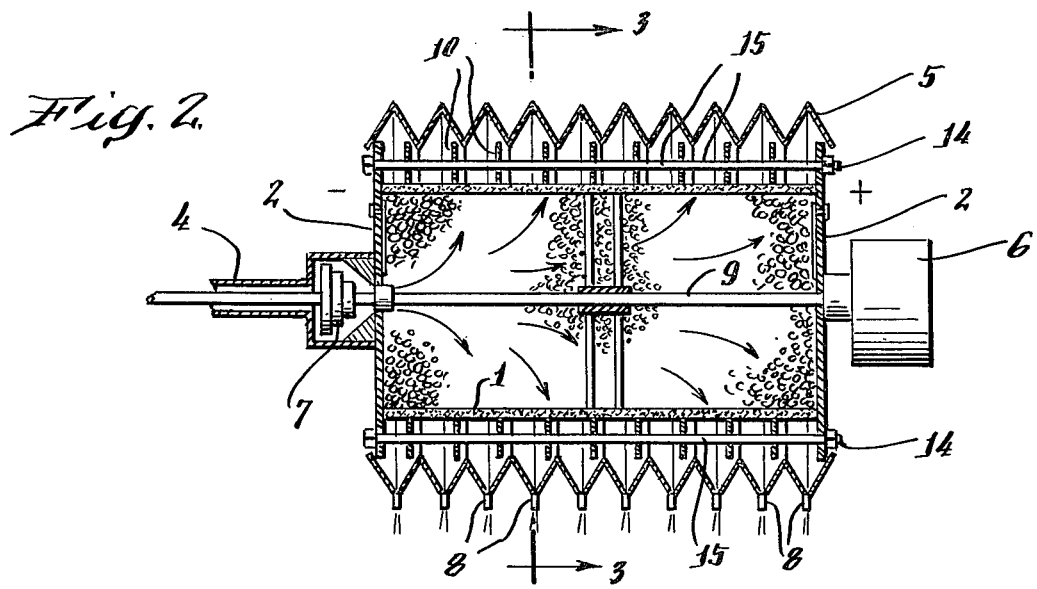

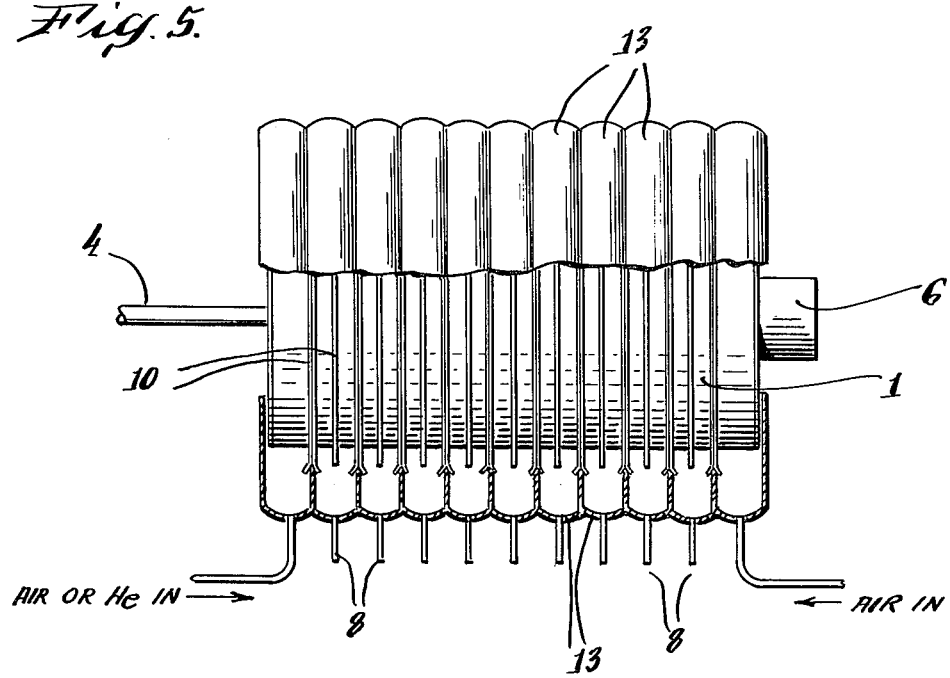
Fig. 5.
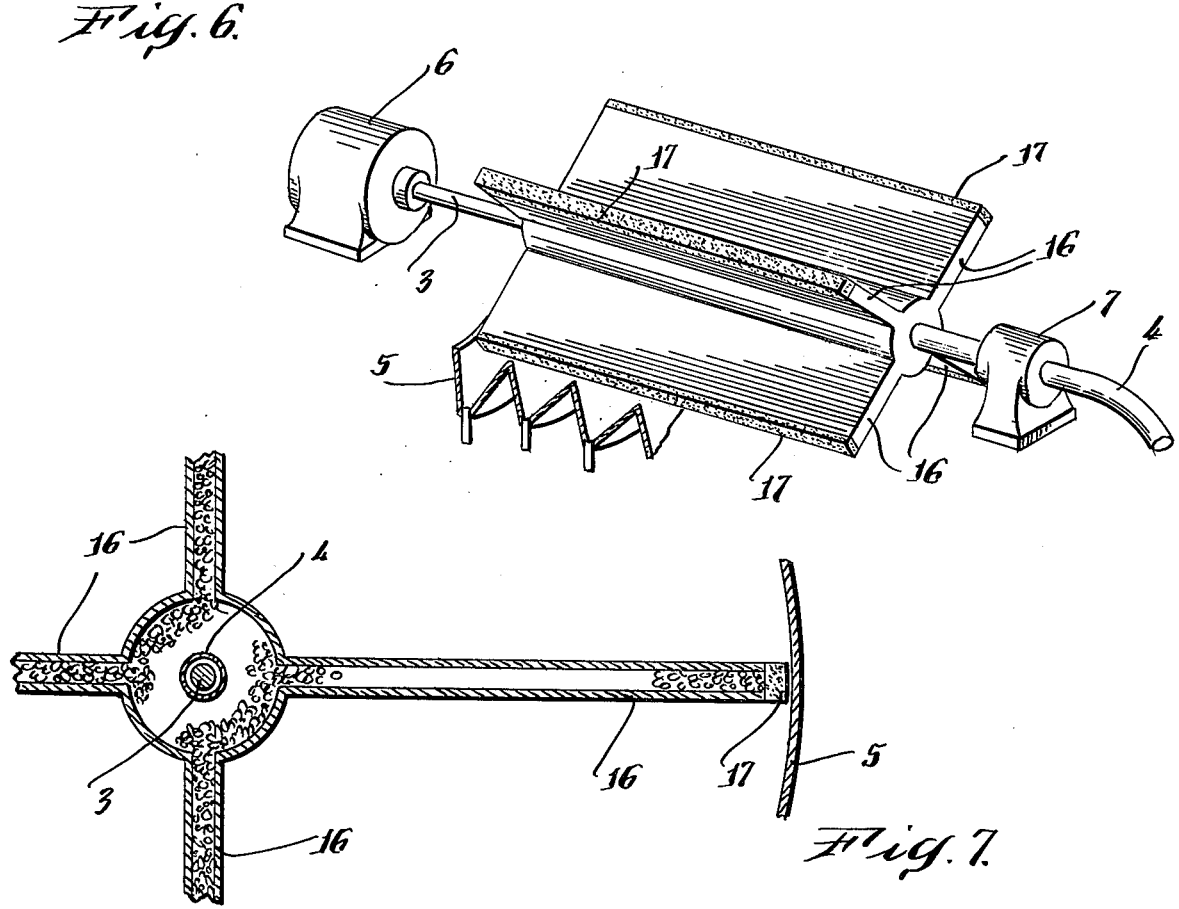
Fig. 6.
Fig. 7.

4,107,041

ELECTROMATOGRAPHIC SEPARATING APPARATUS AND SYSTEM

BACKGROUND OF THE INVENTION

Chromatographic separation of materials, either in liquid or in gas form, is very old, and it is also known to make the process continuous. For example, in Pat. No. 3,076,103, Feb. 12, 1963, to Heaton, a vertical annular chromatographic column is described which is slowly rotated, for example from one to a few revolutions per hour, and materials to be separated, either liquid or gaseous, are introduced in an annular manifold in an upper plate, and at one point samples are removed from a similar annular manifold in a bottom plate. The samples are taken as the materials chromatographically separated reach the bottom manifold, the rate of rotation and annular column height being chosen so that a continuous separation takes place. In this patent, flow through the annular column is only by gravity or, in the case of gas chromatographs, by the gas pressure introducing them. There is no movement by centrifugal force as the rotation is so extremely slow that the centrifugal force is completely negligible.

Continuous separation has also been effected in a circular loop column around which a sample extractor is slowly rotated. This is shown in U.S. Pat. No. 3,062,038, Nov. 6, 1962, to Ayers. Here again, there is no centrifugal force acting on the chromatographic column.

Continuous gas chromatography with a helium eluting gas is also shown in U.S. Pat. No. 3,859,203 on an invention made under a NASA contract and, therefore, owned or controlled by the U.S. Government. The column is horizontal but is not spun to produce centrifugal force.

It has also been proposed to drive gases through a chromatographic column by centrifugal force, some being discharged from an upper outlet and others from a lower. This is described in U.S. Pat. No. 3,016,106, Jan. 9, 1972, to Luft. The centrifugal force is the driving force through the column, and there is no movement through the column with centrifugal force at right angles thereto. A similar column with centrifugal force is described in U.S. Pat. 3,078,647, Feb. 26, 1963, to Mosler.

Electrophoretic separation of materials of suitably different electrophoretic character is also well known, but there has never been described a chromatographic column, with or without electrophoretic action, which is spun rapidly so that particular fractions are removed over short paths by a very substantial centrifugal force moving at right angles to the passage of the materials to be separated through the spinning column.

SUMMARY OF THE INVENTION

The present invention combines continuous chromatographic separation with centrifugal force which removes fractions along an elongated column at a much more rapid rate, preferably at least an order of magnitude greater, than the movement through the column. This is effected by a rapidly spinning chromatographic column, substantially horizontal being preferred for liquid separation. The spinning column generates centrifugal force, which moves samples which are introduced at one end of the column relatively rapidly at different points. The centrifugal force and the path length as compared to the force moving the samples along the column are such that removal of samples along the column is continuously effected at a rate, at each position, very much greater than the motion of the materials through the chromatographic packing.

In the case of liquid separation, a spinning column of porous, filter-grade, ceramic material with impervious ends, which may be metal, is spun rapidly to develop very substantial centrifugal force, and the mixtures to be separated are introduced at one end, preferably under substantial pressure, and move through the column at right angles to the centrifugal force generated. The spinning ceramic column is reinforced by strong rings, for example stainless steel, with flat sides and stationary troughs at the peripheries provided with suitable drain holes. The rings are held together by through-bolts with suitable spacers.

The material to be separated, for example a plurality of proteins, which may be constituents of blood, dissolved or otherwise dispersed in a liquid, is introduced under pressure in one end of the column, desirably in the column. There is a complex combination of factors moving the different materials along the spinning column. For example, one effect is that the momentum of heavier particles is greater than that of lighter particles and, therefore, they move down the column faster. However, since the column is packed with suitable chromatographic particles, the effect of these particles to hold back different constituents is often the primary separating force, and if lighter molecules or aggregates have sizes or shapes such that they are less retarded than the heavier ones, they may move through the column more rapidly and therefore reach a further point along the column. The chromatographic effect is usually greater in magnitude than the effect of momentum, although the latter is still operating and has been mentioned. If the heavier particles are less slowed up by the packing, the effect of their greater momentum opposes the chromatographic separation. The chromatographic effect is so much greater than the effect of momentum that in many cases separation can still be effected. However, optimum separation is effected when the holding back by the chromatographic particles of the heavier constituents will improve separation. However, the lengths of the columns are generally chosen for practical purposes, and a column may be used for separating a number of different materials at different times. Of course, where a spinning column is to be used only in a single separation at all times, its length, relative speed of spinning to force of introduced materials to be separated is chosen and controlled for optimum rate of continuous separation. However, often different materials will be separated at different times, and so a column of suitable length and spun at optimum rate will be used together with the best chromatographic particles for the materials most difficult to separate. In the case of more easily separated materials, the far end of the column may not be acting at all, but in many installations it is much cheaper to have a column of length suitable for the more difficult separations even though in some separations a portion of the column is not actually operating.

It should be noted that when the materials to be separated are dispersed in a solvent, which is very often the case, the solvent performs a dual function, both dispersing the initial material and as an eluting solvent, because in most cases the solvent moves more readily through the chromatographic packing than do the materials to be separated. In such a case, the solvent also acts as an eluting solvent. However, the present invention is useful where liquids to be separated are not dispersed in a separate solvent, and such operations are included within the scope of the invention.

When the materials to be separated have different electrophoretic characteristics, such as polarity, the end plates of the spinning column may be maintained at different potentials so that the electrophoretic effect can add to the chromatographic effect. Of course, the polarity of the plates must be chosen so that the electrophoretic effect does not act against the chromatographic effect.

Electrophoretic action is sensitive to the amount of separation and type of material between the plates, and, in general, there is less effect if there is a very long pathway for a given difference in electrophoretic potential which produces a much smaller gradient. In such cases, rings with electrophoretic plates may be arranged along the length of the spinning column to provide steeper electrophoretic voltage gradient and enhance the electrophoretic separation. In the drawings only a single additional plate, although of course they must be in pairs, is illustrated in a separate figure in order not to confuse the drawing.

In the case of liquid separation, the stationary troughs formed at the peripheries of the supporting rings, with their drainage holes, permit drainage by or assisted by the force of gravity, and the openings in the bottom troughs permit removing portions of the separated materials at different positions along the column. The separation will vary with different materials, and in some cases there will be a separation along the column between individual supporting rings. In this case, the stream draining from the bottom of each trough will go to a separate collecting vessel. In a number of other cases, the same material may come out over a band of substantial width which may include a number of rings. In such cases the drainage from a number of rings is collected by a trough to a single collector. As the number of points from which different samples are to be taken will vary with each system where materials are to be separated by the apparatus of the present invention, the various collectors are not shown in the drawings since it is conventional to apply collectors and the particular design of collector forms no part of the present invention. To show all possible shapes and designs would be impractical, and they are, therefore, not shown.

The above description of separations of materials dispersed or themselves in the liquid phase is equally applicable to gas chromatography. However, in this case, since gravity does not play any significant part in the removal of gaseous constituents along the column, it is not at all necessary that the column, which is spinning, be horizontal. It can be vertical, and its particular orientation is purely a matter of convenient engineering construction. In the drawings, horizontal columns are shown, which are equally applicable for liquid and gas. In the case of gas chromatography, instead of a filter-grade ceramic tube metal tubes may be used, with suitable peripheral rings of openings along the column. This sometimes makes construction more economical as metal tubes are much stronger. Instead of drainage troughs, which have been described in connection with liquid operation, for gas chromatography they are actually manifolds.

In gas chromatography, where there are electrophoretic differences between the gases to be separated, the use of voltage gradient, either a plurality or a single one, as has been described for liquids, may also be used. Since the effect of the electrophoresis, which reinforces the separating power of the chromatographic column, is similar for gases and for liquid, it is not necessary to describe special shapes or forms of the electrophoretic plates or rather spokes.

It should be noted that where electrophoretic action reinforces chromatography it is often possible to use shorter spinning columns because both forces are active. This is illustrated in one of the figures of the drawings.

Because of the rapid removal of samples at the particular points chosen by reason of the centrifugal force at right angles to the column axis, it is often possible to make sharper separations within reasonable times or, expressed another way, through-puts, and so the apparatus and system may be used for large volume and also very fine separations, for example, separations of uranium or thorium isotopes, where the difference in weight as compared to the average weight of the molecules is very small, but their molecular action and polarity are quite different, separation is possible. In such situations the materials may be in the liquid phase, for example in the case of uranium, fluorides or other compounds maintained at temperatures such that they do not volatilize. This is not to say that volatile uranium fluorides may not be used in gas chromatography. However, it is often easier, and frequently the separation sharper, in the liquid phase, and it is an advantage of the present invention that such separations can be made, avoiding the enormous cost of the gaseous diffusion plant. This is another instance of a practical advantages of the present invention.

Still considering isotope separation, the present invention is well suited for the separation of hydrogen from deuterium or tritium because in these cases the molecular weight of the two isotopes as compared to the average weight of the mixture is very high. This makes it easily possible to separate hydrogen from deuterium or light water from heavy water. It is less needed for tritium because that is generally manmade. When water from the oceans or elsewhere is electroyzed to form hydrogen, deuterium gases and oxygen gases, the separation of deuterium from hydrogen can be effected readily by gas chromatography, and what has been stated above with respect to the use of the invention for gas chromatography is applicable, and much more economical separation of deuterium from hydrogen whether in the liquid or gaseous phase is made possible in a continuous manner. At the moment, fusion power with deuterium hydrogen or deuterium-tritium mixtures is still not commercially practical, but it appears likely that it may be so in the not too distant future, and the present invention while not now of practical importance may become so as the fusion plants become a reality.

The columns that have been described have in effect been circular cylinders of the chromatographic material. It is a generally well known effect in chromatography that a long column of small diameter will give sharper separation. However, the capacity of small diameter columns is very small, and so every chromatographic column can be thought of as a compromise between maximum sharpness of separation and volumn of through-put in a unit time. The theory which has been advanced of why sharper separation takes place in a long column of small diameter is that as the materials move through the chromatographic packing they can move in any direction but in a small diameter column they soon hit the wall and are thrown back. In a large column, where there is much more possibility of moving in different directions, this has been called a random walk of the molecules. Of course, the molecules are not capable of making decisions, they operate statistically, but in the small diameter column movement in one direction is stopped fairly quickly and so they move, in general, in more nearly straight lines. It is not desired to tie this invention to a particular theory, although the theory of the random walk has been quite extensively demonstrated. However, theory or no theory, the sharper separation is a well known fact. It is possible to obtain the effects of narrowed dimensions between walls, as in small diameter columns, but still retain a large column which permits reasonable through-puts per unit time. This can be accomplished at a cost of considerably more expensive construction by the column into a series of narrow blades. In other words, if one thinks of a column with solid packing and has a number of blades made by inserting metal walls, the metal walls forming a U-shaped channel which carries the dimension of a large diameter column in between the blades, the material packed in a solid column is omitted. Maximum sharpness of separation can be obtained in columns of modest length by this means, and for many purposes where extreme sharpness of separation is desired the greater expense of construction is well worthwhile.

This is an example of the flexibility of the present invention so that the optimum results for particular operations can be obtained. It might be thought that there would not be a rapid removal of constituents in the particular bands, but since the blades are being spun just as the columns described above, centrifugal force moves the constituents rapidly so that the same rapid removal of constituents at particular points along the column is effected. While the construction is more expensive, there is another offsetting advantage. The U-shaped metal walls are their own reinforcement, so that it is not neccessary to have additional rings. The troughs for collecting, which are stationary, surround the outer periphery swept by the ends of the blades in exactly the same way as described above, and drainage, by gravity when the column of blades is horizontal, or by manifolds in gas chromatography where the column is vertical or inclined, is not changed. There is, incidentally, a smaller volume of chromatographic packing, and this is a further advantage. Not only is the construction somewhat more expensive but balancing of blades is more difficult and must be done more precisely, otherwise the column is restricted to a lower spin rate. These various factors have to be taken into consideration and the best compromise for each particular operation chosen.

BRIEF DESCRIPTION OF THE DRAWINGS

FIG. 1 is a cross-section of a chromatographic column for separation from liquids;

FIG. 2 is a similar cross-section with inlet pump rotating with the column;

FIG. 3 is an elevation of an intermediate electrophoretic plate;

FIG. 4 is a section along the line 4—4 of FIG. 1;

FIG. 5 is a cross-section similar to FIGS. 1 and 2 for a modification for gas chromatography;

FIG. 6 is a perspective of a modification using blades instead of a round cylinder, and FIG. 7 is a cross-section through one blade along the line 7—7 of FIG. 6.

DESCRIPTION OF THE PREFERRED EMBODIMENTS

FIG. 1 is a cross-section of a spinning horizontal chromatographic column especially designed for separation from liquid media. In order not to confuse the drawing, the chromatographic packing which is suitable for the particular separation is shown only at one end of the column. Of course, the whole column is packed with the chromatographic packing material to produce a differential migration process suitable for the particular separation. As the nature of the various chromatographic packings will vary with the materials to be separated and are standard packing, they are shown on the drawings in a somewhat diagrammatic form, as has been indicated.

The column itself is of ceramic material which is porous, of the type used for ceramic filters. This is shown at 1, and the end plates, which may be of metal, are designated 2. A central shaft 3 is connected to a suitable drive, such as an electric motor, (not shown). Surrounding the central shaft is an inlet pipe 4 in which materials to be separated are introduced under fairly high pressure by a pump, which in this figure is also not shown. The ceramic cylinder forming the column is reinforced by stainless steel rings which are shown at 10 held together with longitudinal through-bolts 14 with spacers 15 shown purely diagrammatically. Around the outside periphery of the rings are stationary troughs 5 which receive liquid coming off at particular points along the column. Stationary troughs 5 surround the spinning column at each pair of rings. In the bottom of each trough there are provided drain holes 8, and liquid samples at various points along the column are continuously removed into collectors, which, as they are standard features of equipment, are not shown. As has been stated before, there may be individual collectors for individual rings or a number of rings may have a common collector where the chromatographic separation is in bands of various widths. The widths, of course, will vary with the particular materials being separated, as is well known in batch chromatography.

In FIG. 1 there are indicated diagrammatically paths of particles in the liquid to be separated. If there is a considerable difference in molecular weight of the different materials, the heavier ones would have greater momentums and will move further down the column. The effect of the chromatographic packing, which depends on the chromatographic characteristics of the constituents to be separated, such as, for instance, shape, size, and molecular weight, is normally greater than the separation due to different momentums. These chromatographic effects are well known in batch chromtography where material is pumped through a chromatographic column, and the same results are obtained in the present invention; but with the fairly high pressure inlet and the large amount of centrifugal force which removes the bands rapidly, the width of chromatograph bands will vary considerably from the bands of the same material in a batch chromatograph operating under gravity. Where separation is very rapid, the far end of the spinning column may actually receive no materials to be separated, but where materials are dissolved or otherwise dispersed in a solvent, the solvent may be removed in further portions of the column as the solvent is performing a dual function both of dispersing the materials to be separated and as an eluant.

FIG. 4, which is a cross-section along the line 4—4 of FIG. 1, shows the rings and holes for through-bolts 15. The same reference numerals are used as in FIG. 1, and it will be noticed that FIG. 4 does not show drain holes 8, which are seen in FIGS. 1 and 2.

FIG. 2 is a cross-section similar to FIG. 1 of a shorter column. The end plates are shown as carrying voltages positive in one end and negative in the other. In other words, a voltage gradient appears along the column, and where materials are separated which have different electrophoretic characteristics, this operates to speed up the separation, and this is shown, symbolically, by a shorter column than in FIG. 1. There is also shown the drive motor 6 which drives the central shaft 9, in purely diagrammatic form as it is a standard piece of equipment. At the other end of the shaft, which is at the inlet end of the column, there is a pump 7 which rotates with the spinning column. This simplifies the packing to insure tightness of the inlet tube 4 and is a modification which is of advantage but which is not the basic distinction of the invention from the prior art.

As the electrophoretic effect is dependent on the voltage gradient, it is sometimes desirable to break up the electrophoretic plates so there are several shorter but steeper voltage gradients along the column. FIG. 3 shows one of these intermediate electrophoretic electrodes, which are illustrated as spokes. These intermediate spokes or electrophoretic electrodes are, of course, in pairs, but as they are identical except for the polarity of the voltage applied, only one is shown in FIG. 3. Where there are more than one pair of electrodes, it is necessary that there be insulation provided along the drive shaft so that each electrophoretic anode receives its voltage, through slip rings of conventional design, (not shown).

FIG. 2 indicates a shorter column where electrophoresis reinforces the chromatographic effect of separation and permits a shorter column. For some spinning columns it may be desirable with different materials to be separated to use or not to use the electrophoretic effect. Thus, for example, a longer column, such as is shown in FIG. 1, may be used with the electrophoretic connections as described in connection with FIG. 2 since, of course, the voltage can be cut off by a suitable switch and then the column operates on a pure combination of momentum, chromatographic separation, and continuous centrifugal force removal.

The above description of FIGS. 1 to 4 has been primarily for columns for separation of materials dispersed in a liquid. The principles of the invention can be used for gas chromatography, and FIG. 5 shows a gas chromatographic column in which the column walls are metal, with holes along their periphery. The escaping gaseous materials are carried off in manifolds 13 since, of course, the gases will not drain off under gravity as in the case of liquid. Connections from the manifolds to suitable collectors involves conventional equipment though, of course, the equipment must be suitable for the spinning column. For gas chromatography, if a positive pressure is placed on the end manifolds and a slightly negative pressure on the other manifolds, the gases will not escape to the atmosphere. While this is not the primary feature of the invention, it is a desirable feature for gas chromatography.

In equipment for gas chromatographic separation, it is not necessary that the column be horizontal although this is quite satisfactory and is shown in FIG. 5. The column may be vertical or slanted because the movement of the gases to be separated is not substantially effected by gravity. The gas chromatographic separation may, if desired, be used with an eluant gas, such as, for example, helium, which, of course, is removed in the manifold near the far end of the column is recycled by conventional means. If the separation uses air as an eluant material, it is not necessary to recycle it and the manifolds receiving the air may be vented to the atmosphere.

FIGS. 6 and 7 illustrate a modified spinning column in which instead of the column being a cylinder it is formed of four hollow blades 16 which have ends 17 of porous ceramic material which permit liquids to pass through, just as in FIG. 4. The troughs formed of the four blades and which collect liquid samples are provided with drain holes. The troughs are of the same shape as in FIGS. 1 to 4 and so are given the same reference numeral 5. Also, the motor and pump are given the same reference numerals as the same elements in FIG. 2. The advantages and disadvantages of FIGS. 6 and 7 have been fully discussed in the summary of the invention and, therefore, do not require repeating at this point.

A typical example will follow for separating definite materials and as to be considered only as an illustration without limiting the claims of the application.

EXAMPLE

Tests of molecular separation were made in an experimental system which used a 6-inch inside diameter cylinder 18 inches long made of sintered aluminum oxide that was transfusable to liquids. This cylinder was externally strengthened with stainless steel rings, and the cylinder was loaded with partially loaded ion exchange resin. The resin grain size was controlled. Each grain was round, having a diameter of 0.008 ± 0.0005 inch. This control, by experimental tests, seemed to be very important. The mixed material that was separated was pumped into the rotating cylinder or column at a constant pressure of 150 psi at a constant pH of 6 and temperature of 20° C. The flow entered the center of the column through an opening in the pipe of 0.025 at a high speed. The cylinder was rotated at a controlled speed of from 2000 RPM to 5800 RPM. The separated samples were collected at different points along the outside of the cylinder. Individual samples were collected at different times along this route. These samples were analyzed as to their purity and exclusion of the other materials in the original mix fed into the separator.

A mix was made by dissolving sugar, gelatin, and KCl in 3000 cc. of water. 50 grams of each in dry form was used. Extraction of this mix was made. The gelatin came out first in a band about 3½ wide from the input end. The sucrose came out in a narrow band 6 inches up from the input end. This band was slightly more than an inch wide, with a definite peak. The KCl came out 10 inches up from the input end. This band was 2 inches wide; it also had a definite peak. When performing the above experiment, no electrophoretic effect was in used. The supply voltage was not turned on. When the current was on and set at 340 volts, the collection points were different for KCl and gelatin. The gelatin band was less broad and up further from the input end-dependent on polarity. The KCl was moved 4 inches either up or down by the application of 340 volts.

I claim:

1. A continuous chromatographic column, the column having a length larger than its cross-sectional diameter, in which the column is packed with suitable chromatographic packing, means for introducing the materials to be separated under pressure at one end, means for spinning the column about an axis substantially central to the column at a rate such that the centrifugal force over the relatively short path at right angles to the column axis is very much greater than rate at which materials to be separated move along the column, whereby removal of materials at different points along the column is relatively very rapid, the column walls along its length being provided with means for permitting materials to be separated to pass through readily, and stationary collecting means for receiving the different fractions.

2. A column according to claim 1 for separating materials dispersed in a liquid phase in which the column walls are porous and reinforcing means for the column along its length with rings of strong and relatively corrosion-proof material, the rings being held together, and stationary peripheral troughs will openings through which materials separated can leave, the column being substantially horizontal and spun at a rate, compared to the pressure of inlet of the materials to be separated, so that over the short path at right angles to column axis materials to be separated move at a much more rapid rate than materials move along the column, whereby the chromatographic separation is effected primarily by the long path along the column and separation under centrifugal force results in a very small, chromatographic separation, the column being provided with troughs spaced around the column at predetermined positions to receive materials separated at such points.

3. A continuous spinning chromatographic column according to claim 2 in which a pump is provided to supply material to be separated under pressure, means for rotating it with the column and requires no liquid-tight bearings between the pump and the column.

4. A continuous spinning chromatographic column according to claim 1 in which a pump is provided to supply material to be separated under pressure, means for rotating it with the column and requires no liquid-tight bearings between the pump and the column.

5. A continuous chromatographic column according to claim 4 in which means are provided for establishing at least one voltage gradient along the column, whereby additional separation by electrophoresis is effected.

6. A continuous chromatographic column according to claim 4 in which means are provided for establishing at least one voltage gradient along the column, whereby additional separation by electrophoresis is effected.

7. A continuous chromatographic column according to claim 3 in which means are provided for establishing at least one voltage gradient along the column, whereby additional separation by electrophoresis is effected.

8. A continuous gas chromatographic column according to claim 1, said chromatographic column being a gas chromatographic column, in which manifolds for receiving separated gases are provided at predetermined positions along the column.

9. A gas chromatographic separating apparatus according to claim 8 in which means are provided to establish at least one voltage gradient along the length of the spinning column, whereby separation of gaseous materials having different electrophoretic characteristics is effected.

10. A continuous chromatographic column according to claim 1 in which the column is formed of rotating packed hollow blades, in effect eliminating the packing between them, the blades having transfusable outer edges and stationary collecting means surrounding the rotating blades.

* * * * *